United States Patent
Suwa et al.

(10) Patent No.: US 6,884,819 B1
(45) Date of Patent: Apr. 26, 2005

(54) NEUROPATHY REMEDIES

(75) Inventors: Yorimasa Suwa, Hino (JP); Noboru Yoshioka, Hino (JP); Takami Arai, Hino (JP); Katsutoshi Sakurai, Hino (JP); Jun Suzuki, Hino (JP); Yasuyoshi Watanabe, Minoo (JP); Masaaki Suzuki, Nagoya (JP); Takumi Satoh, Suita (JP); Yumiko Watanabe, Minoo (JP); Yosuke Kataoka, Otsu (JP)

(73) Assignees: Teijin Limited, Osaka (JP); Osaka Bioscience Institute, Osaka (JP)

( * ) Notice: Subject to any disclaimer, the term of this patent is extended or adjusted under 35 U.S.C. 154(b) by 358 days.

(21) Appl. No.: 10/048,964
(22) PCT Filed: Aug. 4, 2000
(86) PCT No.: PCT/JP00/05267
  § 371 (c)(1),
  (2), (4) Date: Feb. 5, 2002
(87) PCT Pub. No.: WO01/10445
  PCT Pub. Date: Feb. 15, 2001

(30) Foreign Application Priority Data

Aug. 5, 1999 (JP) .......................................... 11/222311

(51) Int. Cl.$^7$ .............................................. A01N 37/08
(52) U.S. Cl. ...................................... 514/530; 514/569
(58) Field of Search ................................. 514/530, 569

(56) References Cited

U.S. PATENT DOCUMENTS 5,700,833 A  * 12/1997  Watanabe

FOREIGN PATENT DOCUMENTS

| EP | 0 911 314 A1 | 4/1999 |
|---|---|---|
| JP | 10-87608 | 4/1998 |
| JP | 10-101610 | 4/1998 |
| JP | 11-5764 | 1/1999 |

OTHER PUBLICATIONS

Masaaki Suzuki, et al., "Molecular Design of Prostaglandin Probes in Brain Research: High, Specific Binding to a Novel Prostacyclin Receptor in the Central Nervous system," Bull. Chem. Soc. Japan, May 2000, vol. 73, pp. 1053–1070.
Masaaki Suzuki, et al. "15–Deoxy–16–(m–tolyl)–17, 18, 19, 20–tetranorisocarbacyclin: a simple TIC derivative with potent anti–apototic activity for neuronal cells", Chemical Communications. (Cambridge), (1999), (4), pp. 307–308.
Masaaki Suzuki, et al. "Design of prostaglandins with high binding affinity and selectivity for an IP2 receptor in the central nervous system and their biological activity", Tennen Yuki Kagobutsu Koen Yoshishu, (1998), 40$^{th}$, pp. 145–150.
Masaaki Suzuki, et al., "(15R)–16–m–tolyl–17, 18, 19, 20–tetranorisocarbacyclin: A stable ligand with high binding affinity and selectivity for a prostacyclin receptor in the central nervous system", Agnew, Chem. Int. Ed. Engl. 1996, 35, No. 3, pp. 334–336.

* cited by examiner

Primary Examiner—Paul J. Killos
(74) Attorney, Agent, or Firm—Sughrue Mion, PLLC

(57) ABSTRACT

The present invention provides a neurodegenerative disease therapeutic agent containing as its active ingredient a (15R)-isocarbacycline derivative indicated by the following formula [I] or a 15-deoxy-isocarbacycline derivative indicated by the following formula [III]:

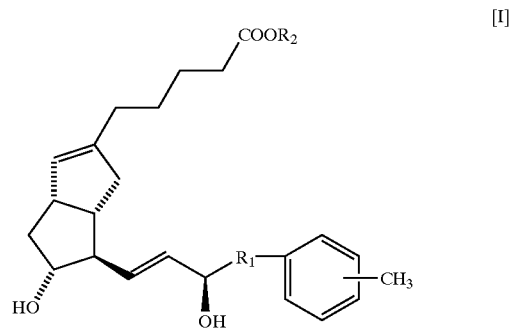

(wherein, $R_1$ represents a $C_1$–$C_6$ alkylene group, and $R_2$ represents a hydrogen atom, a $C_1$–$C_7$ alkyl group or protective group); or,

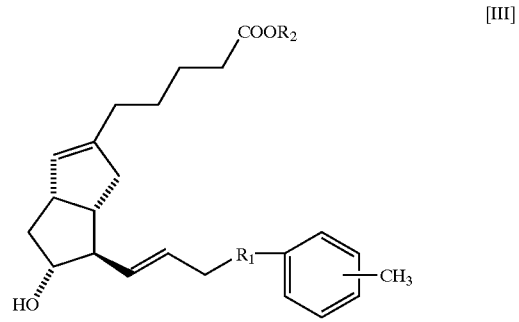

(wherein, $R_1$ and $R_2$ are the same as those defined in formula [I]).

8 Claims, No Drawings

NEUROPATHY REMEDIES

TECHNICAL FIELD

The present invention relates to a neurodegenerative disease therapeutic agent, to a therapeutic agent for degenerative diseases presenting dementia symptoms and, particularly, to an Alzheimer's disease therapeutic agent. More particularly, the present invention relates to a clinically applicable neurodegenerative disease therapeutic agent, to a therapeutic agent for degenerative diseases that present dementia symptoms and, in particular, to an Alzheimer's disease therapeutic agent, that is highly effective in improving learning and memory disorders and has minimal adverse side effects such as toxicity and blood pressure reduction.

BACKGROUND ART

Neurodegenerative disease is the general term for a group of diseases of unknown cause resulting in neural disorders at a specific site. More specifically, examples of degenerative diseases of the cerebrum include Alzheimer's disease, and Pick's disease, examples of degenerative diseases of the cerebral basal ganglia include Parkinson's disease and Huntington's disease, examples of degenerative diseases of the cerebellum include spinocerebellar atrophy, and degenerative diseases of the spinal cord include amyotrophic lateral sclerosis.

Since the cause of these neurodegenerative diseases is unknown, it is difficult to treat them with etiogenic therapy, making it necessary to rely upon nosotropic therapy.

For example, although all of the drugs currently approved for use as therapeutic agents of Alzheimer's disease are acetylcholine nervous system activators, they are nosotropic therapeutic agents developed on the basis of the pathological finding that the acetylcholine nervous system is significantly impaired in Alzheimer's disease patients. In addition, in actual Alzheimer's dementia, it has been demonstrated that the acetylcholine nervous system is not the only system that is impaired, and with respect to this point as well, there thought to be limitations on the effects of acetylcholine nervous system activators.

However, due to the recent progress in disease research at the molecular level, it has been demonstrated that many neurodegenerative diseases share a common characteristic in that neuropathy/cell death is induced by the polymerization and accumulation within the cell of abnormal proteins unique to each disease.

For example, in the brain of an Alzheimer's disease patient, amyloid-like extracellular deposits referred to as senile plaque, and fibrous compounds composed mainly of phosphorylated tau protein (neurofibrillary tangle), are observed in parallel with pathological condition. The major component of senile plaque is an insoluble protein adopting a β sheet structure composed of 40 to 43 amino acid residues referred to as amyloid β protein (Aβ). This protein has been demonstrated to be formed as a result of cleavage in the vicinity of a membrane penetrating region of a membrane protein referred to as amyloid precursor protein (APP). As a result of etiogenic gene analysis of hereditary Alzheimer's disease, since it was found that a mutation occurs in the APP gene itself resulting in increased production of Aβ, or production of Aβ increases due to mutation of the presenilin gene, a different etiogenic gene, and that Aβ extracted from the body or synthesized artificially exhibits toxicity on nerve cells, the idea that the mechanism of occurrence of Alzheimer's disease involves excessively produced Aβ becoming insoluble causing it to be deposited in nerve cells and demonstrate toxicity which in turn causes degeneration is considered to be the most promising.

In addition to Alzheimer's disease, in disorders such as Huntington's disease, spinal and bulbar atrophy, Machado-Joseph's disease, denatorubropallidoluysian atrophy, the accumulation and aggregation of polyglutamine formed due to the elongation of a CAG repeat within the gene, and in prion diseases such as Creutzfeldt-Jakob's disease, the accumulation and aggregation of abnormal protein caused by structural conversion of normal prion protein by some unknown cause, have been determined to be the cause of neuropathy/cell death in each of these diseases. Moreover, in Parkinson's disease and Lewy body disease, the accumulation and deposition of a protein known as α-cynucrein, and in amyotrophic lateral sclerosis, the accumulation and aggregation of a mutant superoxide dismutase, have been indicated has having the potential to cause neuropathy/cell death. In addition, among these, although prion protein and α-cynucrein adopt a β sheet structure in the same manner as Aβ, this has been determined to function as the trigger that causes aggregation and deposition.

Thus, if it were possible to produce a model that expresses a pathological state similar to that of human disease by making abnormal proteins thought to cause these neurodegenerative diseases present in excess in the body of an animal, that model could be considered to be extremely useful in terms of developing etiogenic therapy for neurodegenerative diseases.

Attempts have previously been made to produce an animal model of Alzheimer's disease either by producing Aβ in excess in an animal body by transgenic mouse technology, or by inducing a disorder by directly injecting Aβ into the brain of a normal animal. For example, decreased learning and memory ability has been reported by implanting a miniaturized osmotic pressure pump beneath the skin of the back of a normal rat for the purpose of continuous infusion of β protein into the ventricle, (Neuroscience Letters, Vol. 170, pp. 63–66, 1994). This β protein ventricular infusion model is the most suitable as a system for evaluating Alzheimer's disease therapeutic agents used for the purpose of etiogenic therapy.

On the other hand, prostaglandin (PG) compounds are known to have various physiological activities, including potent platelet aggregation inhibitory action, vasodilation and its accompanying blood pressure lowering action, gastric acid secretion inhibitory action, smooth muscle contractile action, cell protective action and diuretic action. Numerous attempts have been made to develop natural PG present in the body, or PG derivatives synthesized in the form of their agonists, as pharmaceuticals based on these physiological activities, and some of those attempts have lead to pharmaceuticals that have actually been marketed commercially.

Among PG, natural prostacyclins are locally acting hormones produced primarily in the vascular endothelium in the body, and attempts have been made to use them directly as pharmaceuticals by utilizing their potent physiological activity such as platelet aggregation inhibitory action and vasodilatory action (P. J. Lewis, J. O. Grady, Clinical Pharmacology of Prostaglandin). However, since natural prostacyclins have an enol-ether bond within their molecules that is susceptible to hydrolysis, they have the problem of being easily deactivated under neutral or acidic conditions, thereby preventing them from being preferable compounds for use as pharmaceuticals due to their chemical instability. Thus, research has been conducted on the synthesis of chemically stable synthetic prostacyclin derivatives that exhibit similar activity to that of natural prostaglandins (Synthesis, 1984, 449, Japanese Unexamined Patent Publication No. 61-129146). 9(O)-methano-$\Delta^{6(9\alpha)}$-prostaglandin $I_1$ (isocarbocyclines) has been synthesized that adequately satisfies chemical stability by substituting methine groups (—CH=) for the oxygen atoms at the $6^{th}$ and $9^{th}$ positions of prostacycline (Japanese Unexamined Patent Publication No. 59-210044), and this compound has demonstrated potent platelet aggregation inhibitory action, vasodilatory blood pressure lowering action and other biological activities comparable to natural prostaglandins (Japanese Unexamined Patent Publication No. 59-210044, Japanese Unexamined Patent Publication No. 61-197518).

In the past however, development of PGs as pharmaceuticals has primarily taken place in the obstetrics and gynecology, cardiovascular and gastrointestinal fields. In addition, they have also been indicated as being useful as oral therapeutic agents for diabetes (Japanese Unexamined Patent Publication No. 2-167227). However, PG compounds also have the potential for being useful as pharmaceuticals in the field of neurology and psychiatry.

Namely, $PGD_2$, $PGE_1$ or the isocarbacycline derivative mentioned above has been shown to demonstrate cerebral protective action on animals in a hypoxic state (Japanese Unexamined Patent Publication No. 60-146826, Japanese Unexamined Patent Publication No. 4-187637, Brain Research, Vol. 769, pp. 321–328, 1997).

In addition, it has also been reported that $PGD_2$, $PGE_1$, $PGE_2$ or $PGF_{2\alpha}$ has a process extension promoting action on neuroblastoma cells (Bulletin of the Japanese Society for Neurochemistry, Vol. 24, 376, 1985; Japanese Pharmacology and Therapeutics, Vol. 21, 37, 1993), that $PGI_2$ and $PGE_2$ have a protective action on primary cultured nerve cells (Neuroscience Letters, Vol. 160, 106, 1993); Brain Research, Vol. 663, 237, 1994), and that $PGD_2$, $PGJ_2$ and so forth have an action that promotes production of nerve growth factor (Japanese Unexamined Patent Publication No. 7-291867).

However, none of these reports specifically indicate the potential for PGs being able to be used as therapeutic agents for neurodegenerative diseases.

However, in the case of attempting to develop a pharmaceutical in the field of neurology and psychiatry, there are problems resulting from the diverse actions possessed by PGs as described above causing adverse side effects, and in order to solve these problems, it is necessary to obtain a compound that acts as specifically as possible on the brain and nervous system. In addition, another problem is the vascular system of the brain restricting the permeability of certain compounds due to the presence of the so-called blood-brain barrier, and in order to develop a PG as a pharmaceutical, it is necessary to enhance the permeability of that PG through the blood-brain barrier.

Therefore, as a result of conducting an in vitro autoradiographic evaluation in a large coronal section of the cerebral hemisphere of Japanese monkeys using a labeled prostacyclin derivative ([$^3$H]iloprost-Schering), the inventors of the present invention found prostacyclin bonding sites in the striatum, amygdala nucleous, hippocampus and a portion of the cerebral cortex. In addition, the [$^3$H]iloprost binding sites found here differed from the binding sites of [$^3$H]$PGE_2$, and $PGE_2$ and $PGE_1$ were determined to recognize the same receptors. In platelets, iloprost binding sites also react with $PGE_1$, and are known to be completely different from $PGE_2$ receptors.

During the course of the above research, a novel $PGI_2$ receptor has been determined to exist in the central nervous system (Neuroscience, Vol. 65, pp. 493–503, 1995), and certain of the inventors of the present invention found several types of isocarbacycline derivatives that function as specific ligands of this novel $PGI_2$ receptor present in the central nervous system (Japanese Unexamined Patent Publication No. 8-245498, Japanese Unexamined Patent Publication No. 10-87608, Japanese Unexamined Patent Publication No. 10-10610, Japanese Unexamined Patent Publication No. 11-5764 and Journal of Neurochemistry, Vol. 72, pp. 2583–2592, 1999). These isocarbacycline derivatives have demonstrated protective action on cultured nerve cells and animal cerebral nerve cells in a hypoxic state (EP-911314).

On the other hand, it has been reported that stability can be improved by formulating $PGE_1$, $PGA_1$ or the above isocarbacycline derivative as a lipid microshere preparation (Japanese Unexamined Patent Publication No. 58-222014, Japanese Unexamined Patent Publication No. 59-141518 and Japanese Unexamined Patent Publication No. 61-289034). Moreover, penetration to the brain when administered into the blood has been shown to increase by formulating the methyl ester of the isocarbacycline derivative as a lipid emulsion (J. Pharm. Pharmacol., Vol. 48, pp. 1016–1022, 1996).

DISCLOSURE OF THE INVENTION

The object of the present invention is to provide a clinically applicable neurodegenerative disease therapeutic agent, a therapeutic agent for degenerative diseases that present dementia symptoms and, particularly, an Alzheimer's disease therapeutic agent having high learning and memory disorder improvement action and minimal adverse side effects such as toxicity and blood pressure lowering action for use as a neurodegenerative disease therapeutic agent, therapeutic agent for degenerative diseases that present dementia symptoms, and particularly an Alzheimer's disease therapeutic agent.

As a result of repeatedly conducting earnest research based on the above problems, the inventors of the present invention first found that by using an evaluation system an animal model of Alzheimer's disease by continuous intraventricular β-amyloid infusion, specific isocarbacycline derivatives that are specific ligands of a novel $PGI_2$ receptor present in the central nervous system have the action of improving learning and memory disorders caused by β-amyloid protein, and that these compounds have hardly any effect on the peripheral cardiovascular system, and that their action is highly brain-specific, thereby leading to completion of the present invention.

Namely, the present invention is a neurodegenerative disease therapeutic agent containing as its active ingredient a (15R)-isocarbacycline derivative indicated with the following formula [I]:

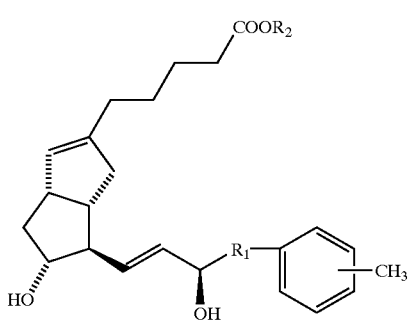

[I]

(wherein, $R_1$ represents a $C_1$–$C_6$ alkylene group, and $R_2$ represents a hydrogen atom, a $C_1$–$C_7$ alkyl group or protective group), a neurodegenerative disease therapeutic agent containing as its active ingredient a 15-deoxy-isocarbacycline derivative indicated with the following formula [III]:

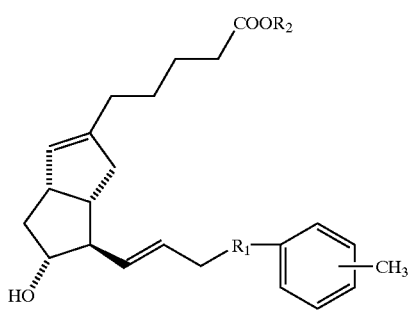

[III]

(wherein, $R_1$ and $R_2$ are the same as defined in formula [I]), a neurodegenerative disease therapeutic agent in which the above neurodegenerative disease is a degenerative disease that presents dementia symptoms, and a neurodegenerative disease therapeutic agent in which said neurodegenerative disease is Alzheimer's disease.

BEST MODE FOR CARRYING OUT THE INVENTION

In the above formulas [I] and [III], $R_1$ is a $C_1$–$C_6$ alkylene group, and more specifically, a linear or branched alkylene group such as that represented with —$(CH_2)_n$— (wherein, n represents an integer of 1 to 6), and n is preferably 1 to 4, and particularly preferably 1. In the above formulas [I]and [III], although the substitution position of the methyl group on the tolyl group on the omega chain may be the ortho position, meta position or para position, the meta position is preferable.

$R_2$ represents a hydrogen atom, a $C_1$–$C_7$ alkyl group or a protective group. Specific examples of a $C_1$–$C_7$ alkyl group include linear or branched alkyl groups such as a methyl group, an ethyl group, an n-propyl group, an iso-propyl group, an n-butyl group, a sec-butyl group, a tert-butyl group or an n-pentyl group.

Examples of $R_2$ protective groups are represented by a pharmaceutically acceptable salt or ester. Specific examples of salts include, as acid addition salt, mineral acid salts such as chloride, bromide, iodide, phosphate, nitrate and sulfate, organic sulfonates such as methanesulfonate, 2-hydroxyethanesulfonate and p-foluenesulfonate, organic carboxylates such as acetate, trifluoroacetate, propionate, oxalate, malonate, succinate, glutarate, adipate, tartrate, maleate, malate or mandelate, and as salt of base, organic sulfonates such as methanesulfonate, 2-hydroxyethanesulfonate and p-toluenesulfonate, salts of inorganic bases such as sodium salt, potassium salt, magnesium salt, calcium salt and aluminum salt, and salts of organic bases such as methylamine salt, ethylamine salt, lysine salt and ornithine salt. In addition, examples of esters include $C_1$–$C_5$ alkyl esters, specific examples of which include methyl ester and ethyl ester.

Preferable examples of the compound in the above formula [I] include (15R)-16-(m-tolyl)-17,18,19,20-tetranorisocarbacycline represented with the following formula [III] and its methyl ester form.

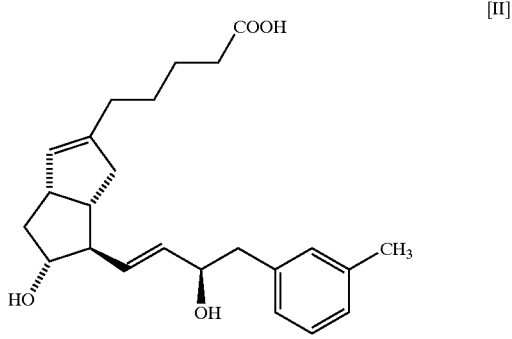

[II]

In addition, preferable examples of the compound in the above formula [III] include 15-deoxy-16-(m-tolyl)-17,18,19,20-tetranorisocarbacycline represented with the following formula [IV] and its methyl ester form.

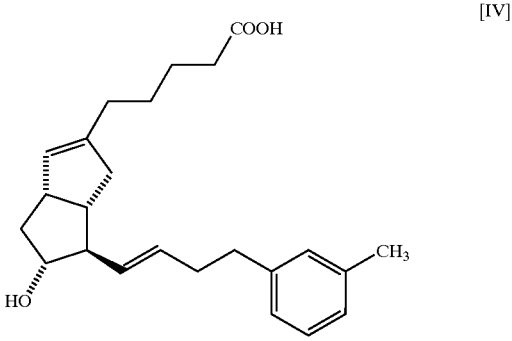

[IV]

The compounds of these formulas [I] through [IV] can be produced according to the method disclosed in Japanese Unexamined Patent Publication No. 8-245498 or Japanese Unexamined Patent Publication No. 11-5764 previously filed by certain of the inventors of the present invention.

Although there are no particular restrictions on the application target of the neurodegenerative disease therapeutic agent of the present invention, it is particularly useful for mammals, and can be used especially preferably for livestock, laboratory animals, pets and humans. Although there are no particular restrictions on the target diseases provided it is a disease that is caused by neurodegeneration, it is specifically effective in application to degenerative diseases that present dementia symptoms such as Alzheimer's disease and Pick's disease, and application to Alzheimer's disease is particularly effective.

Although there are no particular restrictions on the administration method, preferable examples of administration methods include oral administration, percutaneous administration, nasal administration, intravenous administration, intraperitoneal administration, intrarectal administration and intraventricular administration. When clinically applying the isocarbacycline derivative used in the present invention or its clathrate compound, the isocarbacycline derivative as the active ingredient is preferably prepared in the form of a pharmaceutical composition comprised of a pharmaceutically acceptable carrier such as a solid or liquid, followed by the addition of a diluent, namely an additive such as a vehicle or stabilizer, as necessary. An injectable administration preparation of the isocarbacycline derivative of the present invention to be used for therapeutic administration must normally be in a sterile state. Sterility is achieved easily by filtering through a sterilization filtration membrane such as a membrane filter having a pore size of 0.2 μm.

In the above pharmaceutical composition, the ratio of the above active ingredient to the carrier component can be varied between, for example, 0.000001–90% w/w. Although dependent upon the administration method, age, target disease and so forth, the therapeutically effective dosage can be 0.01 μg–1000 mg/day/person, and preferably 0.01 μg–10 mg/day/person. The absorption efficiency into the body is preferably determined individually for each compound according to well known pharmacological methods with respect to each administration route.

Examples of dosage forms and administration forms include oral administration using a dosage form such as granules, grains, powders, pills, tablets, capsules or liquids, and parenteral administration using a local preparation such as suppositories, aerosols, ointments and skin patches. Administration may also be performed by intravenous administration, intraarterial administration, intramuscular administration and subcutaneous administration using an injectable preparation. In addition, an injectable powder may also be used by preparing at the time of use. Moreover, administration may also be performed by nasal administration, intraperitoneal administration, intrarectal administration or intraventricular administration.

Pharmaceutical organic or inorganic and solid or liquid carriers or diluents suitable for oral, enteric or parenteral administration can be used for preparing the isocarbacycline derivative as claimed in the present invention in the form of a pharmaceutical preparation.

Examples of typical carriers or diluents that can be incorporated in tablets, capsules and so forth include binders such as acacia, cornstarch and gelatin, vehicles such as microcrystalline cellulose, disintegration agents such as cornstarch and alginic acid, lubricants such as magnesium stearate, and sweeteners such as sucrose and lactose. In the case the dosage form is a capsule, a liquid carrier such as fatty oil may be contained in addition to the above substances. Various types of other substances can be used as coating agents or agents for improving physical properties in dosage units. Sterile compositions for injection can be formulated in accordance with conventional pharmacological methods. For example, it is preferable to dissolve or suspend the active compound in a vehicle such as water or natural vegetable oil or a synthetic fat vehicle such as ethyl oleate. Buffers such as citrate, acetate and phosphate buffers as well as antioxidants such as ascorbic acid can also be incorporated in accordance with allowed pharmaceutical methods.

In preparing in the form of tablets, tablets can be formed in accordance with routine methods using a vehicle such as lactose, starch or crystalline cellulose, a binder such as carboxymethyl cellulose, methyl cellulose or polyvinyl pyrrolidone, and a disintegration agent such as sodium alginate, sodium bicarbonate or sodium lauryl sulfate.

Pills, powders and granules can be similarly formed in accordance with routine methods using the above vehicles and so forth. Liquids and suspensions can be formed in accordance with routine methods using glycerin esters such as tricaprilin and triacetin or alcohols such as ethanol. Capsules are formed by filling granules, powders or liquids into gelatin or other capsules.

In the case of preparations for oral administration, the isocarbacycline derivative as claimed in the present invention can be converted to a cyclodextrin clathrate compound. Clathrate compounds are prepared by adding a solution in which cyclodextrin has been dissolved in water and/or an organic solvent that mixes easily with water to a solution in which isocarbacycline has been dissolved in an organic solvent that mixes easily with water. The target cyclodextrin clathrate compound is then isolated by heating the mixture followed by concentrating under reduced pressure, filtering while cooling or separating the product by decantation. The ratio of organic solvent and water varies according to the solubility of the starting materials and product. It is preferable that the temperature within the cyclodextrin clathrate compound preparation does not exceed 70° C. α-, β- and γ-cyclodextrin or mixtures thereof can be used to prepare a cyclodextrin clathrate compound. The stability of isocarbacyclines can be improved by converting to a cyclodextrin clathrate compound.

Examples of dosage forms for subcutaneous, intramuscular or intravenous administration include injectable preparations in the form of an aqueous or non-aqueous solution. Physiological saline, for example, is used for aqueous solutions. Propylene glycol, polyethylene glycol, olive oil, ethyl oleate and so forth are used for non-aqueous solutions, and antiseptics, stabilizers and so forth are added to these as necessary. Injectable preparations are sterilized by suitably performing procedures such as filtering through a bacteria capturing filter or blending in a disinfectant and so forth.

Examples of dosage forms for percutaneous administration include ointments and creams. Ointments are formed in accordance with routine methods using oils such as castor oil and olive oil or Vaseline, while creams are formed in accordance with routine methods using emulsifiers such as fatty oil, diethylene glycol and sorbitan monofatty acid ester.

Ordinary suppositories such as soft gelatin capsules are used for rectal administration.

Preparations for parenteral administration can also be administered as an emulsion. Namely, fat emulsions prepared by adding water to a uniform solution of vegetable oil such as soy bean oil, phospholipid such as lecithin and isocarbacycline as claimed in the present invention followed by homogenizing with a homogenizer such as a pressure spraying homogenizer or ultrasonic homogenizer, can also be used as injectable preparations.

Although the following provides a more detailed explanation of the present invention through examples, the present invention is not limited in any way to these examples.

EXAMPLES

Test compounds A through C and comparative test compound D used in the following examples are the compounds indicated below.

Test Compound A:
(15R)-16-(m-tolyl)-17,18,19,20-tetranorisocarbacycline
Test Compound B:
(15R)-16-(m-tolyl)-17,18,19,20-tetranorisocarbacycline methyl ester
Test Compound C:
15-deoxy-16-(m-tolyl)-17,18,19,20-tetranorisocarbacycline methyl ester
Comparative Test Compound D:
(15S)-16-(m-tolyl)-17,18,19,20-tetranorisocarbacycline methyl ester Reference Example 1

Measurement Method of Learning and Memory Ability of Rats by a Step-Through Passive Evasion Test A step-through passive evasive reaction apparatus composed of two chambers separated by a guillotine door, was used for the experimental apparatus. Namely, one of the chambers was a bright chamber composed of clear acrylic boards (floor: 15 cm×25 cm, height: 15 cm) while the other chamber was a dark chamber (of the same size) composed of black acrylic boards. In addition, stainless steel grids having a diameter of 4 mm were provided at intervals of 15 mm on the floor of the dark room, and connected to a shock generator for applying an electric shock.

To begin with, after opening the guillotine door and allowing to freely explore the inside of the apparatus for 1 minute, the door was closed, the rat was placed in the bright chamber as an acquisition trial and the door was opened 30 seconds later. The door was closed after all four limbs of the rat entered the dark chamber followed immediately by the application of an electric shock. The intensity of the electric shock was set at 0.5 mA for 5 seconds. Subsequently, the rat was immediately placed in the bright chamber and training was repeated while following the same procedure until the rat remained in the bright chamber for 120 seconds even if the guillotine door was opened. As a retention trial conducted 24 hours after the acquisition trial, the rat was placed in the bright chamber and the amount of time until all four limbs entered the dark chamber after the guillotine door was opened 30 seconds later was measured (step-through latency). The maximum observation time during the retention trial was set at 300 seconds.

Reference Example 2

Production of a Alzheimer's Dementia Animal Model by Continuous Intraventricular Infusion of β Protein Seven-week-old, male Wistar rats (body weights: 220–250 g) were used (N=5–10).

β-amyloid protein (1-40) or β-amyloid protein (1-42) was dissolved in 35% acetonitrile/0.1% TFA, injected into a mini-osmotic pressure pump (volume: 230 μl, 0.5 μl/hour) at the rate of 300 pmol/day, and then connected with a dental injection needle by means of a polyethylene tube. For the control group, a pump was connected and injected with β-amyloid protein (40-1). After anesthetizing the rats with pentobarbital (50 mg/kg, i.p.), an incision was made in the skin on the head and a hole was drilled in the cranium with a microdrill in accordance with the brain map. The injection needle was inserted sp that the tip of the needle entered the later ventricle (A=−0.3 mm, L=1.2 mm, H=4.5 mm), and immobilized with dental cement. An osmotic pressure pump was embedded beneath the skin on the back.

Taking the day on which the procedure for embedding the mini-osmotic pump beneath the skin to be day 0, passive evasion tests were conducted on days 13 and 14 in accordance with the method indicated in Reference Example 1. As a result, learning and memory ability was confirmed to have decreased in the β-amyloid protein (1-40) or β-amyloid protein (1-42) dose group as compared with the β-amyloid protein (40-1) dose group.

Reference Example 3

Toxicity Study Method

Thirty-five six-week-old, male C57BL mice were divided into 7 groups as shown in Table 1 below.

TABLE 1

| Administered substance | Dosage mg/kg | Dosing solution volume ml/kg | Dosing solution concentration mg/ml | No. of animals |
| --- | --- | --- | --- | --- |
| Solvent only | 0 | 5 | 0 | 5 |
| Test compound B | 0.03 | 5 | 0.006 | 5 |
| Test compound B | 0.3 | 5 | 0.06 | 5 |
| Test compound B | 3 | 5 | 0.6 | 5 |
| Test compound C | 0.03 | 5 | 0.006 | 5 |
| Test compound C | 0.3 | 5 | 0.06 | 5 |
| Test compound C | 3 | 5 | 0.6 | 5 |

The test compound solutions were administered into the caudal vein at the rate of about 5 ml per minute. The general condition of each animal was suitably observed immediately before and immediately after dosing on the day of dosing, and at 15 minutes, 30 minutes, 60 minutes, 2 hours, 4 hours and 6 hours after dosing. Moreover, the animals were observed for general condition once in a day in the morning from the day after dosing through day 14. In addition, body weights were measured immediately before dosing and on days 1, 3, 7 and 14 after dosing.

Reference Example 4

Measurement Method of Blood Pressure Lowering Action

Thirty five, male Wistar rats. (body weights: 230–270 g) were divided into 7 groups as shown in Table 2 below.

TABLE 2

| Administered substance | Dosage mg/kg | Dosing solution volume ml/kg | Dosing solution concentration mg/ml | No. of animals |
| --- | --- | --- | --- | --- |
| Solvent only | 0 | 5 | 0 | 5 |
| Test compound B | 0.03 | 5 | 0.006 | 5 |
| Test compound B | 0.3 | 5 | 0.06 | 5 |
| Test compound B | 3 | 5 | 0.6 | 5 |
| Comp. test compound D | 0.03 | 5 | 0.006 | 5 |
| Comp. test compound D | 0.3 | 5 | 0.06 | 5 |
| Comp. test compound D | 3 | 5 | 0.6 | 5 |

Cannulas were inserted into the left carotid artery for measuring blood pressure, and into the left jugular vein for intravenous injection of the test compounds, respectively. After being housed normally in their cages overnight following surgery, the animals were injected with the test solutions without anesthesia. Blood pressure and heart rate were measured immediately before dosing (0 minutes) and at 5, 30, 60, 120 and 240 minutes after dosing. The blood pressure at 0 minutes for each animals was assigned a value of 100, and measured values of blood pressure at each time were then normalized based on that value.

Example 1

Measurement of Learning and Memory Ability Improvement Effect

The learning and memory ability improvement action of test compound A was measured using the evaluation methods of Reference Examples 1 and 2. Test compound A was dissolved in phosphate-buffered physiological saline and injected using an osmotic pressure pump in the same manner as injection of β-amyloid protein. Test compound A was dissolved in β-amyloid protein solution and injected simultaneous to β-amyloid protein using an osmotic pressure pump.

TABLE 3

|  | Time until moved to dark chamber during retention trial Mean ± standard error (units: sec.) |
|---|---|
| β-amyloid protein (40-1) 300 pmol/day dose group | 272.1 ± 18.3 (n = 8) |
| β-amyloid protein (1-42) 300 pmol/day dose group | 192.5 ± 27.4 (n = 11) |
| β-amyloid protein (1-42) 300 pmol/day + test compound A 1.2 fmol/day dose group | 265.7 ± 32.6 (n = 6) |
| β-amyloid protein (1-42) 300 pmol/day + test compound A 12 fmol/day dose group | 261.8 ± 26.7 (n = 11) |
| β-amyloid protein (1-42) 300 pmol/day + test compound A 120 fmol/day dose group | 276.1 ± 17.0 (n = 10) |

In other words, in this study, test compound A exhibited action that improved learning and memory ability. In particular, in those animals of the test compound 12 fmol/day dose group and 120 fmol/day dose group, the amount of time until the animals moved into the dark chamber increased significantly as compared with the group dosed with β-amyloid protein (1-42) only (p>0.05).

Example 2

Toxicity Study

Ace A toxicity study was conducted on test compounds B and C. As a result, none of the animals died in any of the groups. In the case of test compound B, although decreased movement was observed in the 3 mg/kg dose group starting immediately after dosing, the change was extremely mild and disappeared by 30 minutes after dosing. In the case of test compound C, there were no abnormalities observed in any of the groups. Moreover, there were no abnormalities observed in any of the groups for both test compounds B and C starting on the day after dosing. In addition, there were also no significant fluctuations in body weights for test compound B or C.

In other words, both test compounds were clearly determined to have extremely low toxicity.

Example 3

Measurement of Blood Pressure Lowering Action

Fluctuations in blood pressure following administration of test compound B and comparative test compound D were as shown in Table 4 below.

TABLE 4

| | | Blood pressure (mmHg, ± standard error) | | | | | |
|---|---|---|---|---|---|---|---|
| Admin. substance | Dosage mg/kg | 0 min. | 5 min. | 30 min. | 60 min. | 2 hr. | 4 hr. |
| Solvent only | 0 | 100 | 104.9 (3.0) | 103.9 (2.3) | 107.5 (1.3) | 108.5 (2.0) | 106.7 (2.5) |
| Test comp. B | 0.03 | 100 | 105.8 (2.7) | 103.4 (3.0) | 103.6 (2.9) | 104.5 (3.7) | 100.5 (4.7) |
| Test. Comp. B | 0.3 | 100 | 92.9 (2.2) | 97.7 (2.3) | 97.7 (2.7) | 98.5 (3.0) | 98.0 (5.0) |
| Test comp. B | 3 | 100 | 80.4 (3.9) | 99.4 (3.6) | 101.9 (2.2) | 102.7 (2.3) | 101.0 (2.5) |
| Comp. test comp. D | 0.03 | 100 | 88.9 (7.8) | 92.1 (2.6) | 96.5 (3.0) | 97.3 (1.8) | 99.0 (3.3) |
| Comp. test comp. D | 0.3 | 100 | 49.6 (2.0) | 78.5 (3.8) | 94.4 (2.0) | 93.3 (2.2) | 99.3 (3.0) |
| Comp. test comp. D | 3 | 100 | 55.0 (1.2) | 60.0 (1.9) | 81.1 (4.3) | 103.8 (3.4) | 115.4 (3.7) |

In addition, the fluctuations in heart rate following administration of test compound B and comparative test compound D were as shown in Table 5.

TABLE 5

| | | Heart rate (standard error) | | | | | |
|---|---|---|---|---|---|---|---|
| Admin. substance | Dosage mg/kg | 0 min. | 5 min. | 30 min. | 60 min. | 2 hr. | 4 hr. |
| Solvent only | 0 | 100 | 111.2 (3.4) | 111.5 (5.5) | 110.4 (2.4) | 111.4 (3.5) | 111.2 (2.6) |
| Test comp. B | 0.03 | 100 | 114.8 (6.7) | 123.8 (6.4) | 110.9 (3.4) | 103.8 (2.2) | 100.5 (4.0) |
| Test. Comp. B | 0.3 | 100 | 112.2 (4.2) | 108.4 (2.9) | 101.6 (5.2) | 104.7 (5.5) | 112.0 (5.7) |
| Test comp. B | 3 | 100 | 135.0 (4.8) | 122.7 (4.6) | 102.5 (4.1) | 101.4 (5.8) | 102.2 (6.4) |
| Comp. test comp. D | 0.03 | 100 | 135.5 (4.3) | 113.7 (1.8) | 106.1 (2.5) | 102.9 (3.4) | 104.3 (2.1) |
| Comp. test comp. D | 0.3 | 100 | 127.0 (2.0) | 109.1 (1.7) | 96.3 (3.6) | 97.0 (3.0) | 94.4 (2.5) |
| Comp. test comp. D | 3 | 100 | 124.9 (8.1) | 142.7 (5.2) | 131.0 (6.7) | 104.7 (6.5) | 104.1 (5.1) |

Although test compound B caused a decrease in blood pressure and an increase in heart rate immediately after dosing in the 3 mg/kg dose group, the blood pressure and the heart rate recovered rapidly, the blood pressure, in particular, only demonstrating a mild decrease at 5 minutes after dosing, and both parameters were observed to return to normal at 30 minutes after dosing. There were no significant fluctuations observed in the 0.3 and 0.03 mg/kg dose groups.

On the other hand, in the case of comparative test compound D, decreased blood pressure was observed to continue for 30 minutes or more in the 3 mg/kg and 0.3 mg/kg dose groups.

Namely, test compound B was clearly determined to have an extremely mild effect on the circulatory system.

INDUSTRIAL APPLICABILITY

The therapeutic agent containing as active ingredient a specific isocarbacycline derivative of the present invention is a clinically applicable neurodegenerative disease therapeutic agent, therapeutic agent for degenerative diseases that present dementia symptoms and, in particular, an Alzheimer's disease therapeutic agent, that is highly effective in improving learning and memory disorders and has minimal adverse side effects such as toxicity and blood pressure lowering effects, which can be used as a neurodegenerative disease therapeutic agent, therapeutic agent for degenerative diseases that present dementia symptoms, and in particular an Alzheimer's disease therapeutic agent.

What is claimed is:

1. A method of treating neurode generative disease, said method comprising administering to a subject in need of treatment an effective amount of a (15R)-isocarbacycline compound represented by the following formula [I]:

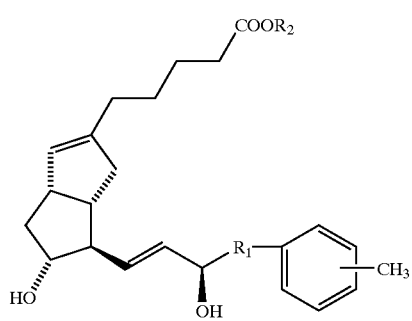

wherein, $R_1$ represents a $C_1$–$C_6$ alkylene group, and $R_2$ represents a hydrogen atom, a $C_1$–$C_7$ alkyl group or a protective group.

2. A method of treating neurodegenerative disease according to claim 1, said method comprising administering to a subject in need of treatment an effective amount of a (15R)-16-m-tolyl)-17,18,19,20-tetranorisocarbacycline represented by the following formula [II] or its methyl ester form:

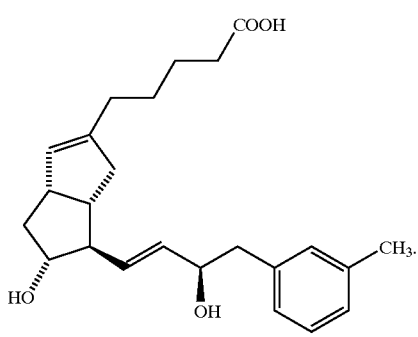

3. A method of treating a neurodegenerative disease according to claim 1 or 2, wherein said neurodegenerative disease is a degenerative disease that presents dementia symptoms.

4. A method of ting a neurodegenerative disease according to claim 1 or 2, wherein said neurodegenerative disease is Alzheimer's disease.

5. A method of treating neurodegenerative disease, said method comprising administering to a subject in need of treatment a 15-deoxy-isocarbacycline compound represented by the following formula [III]:

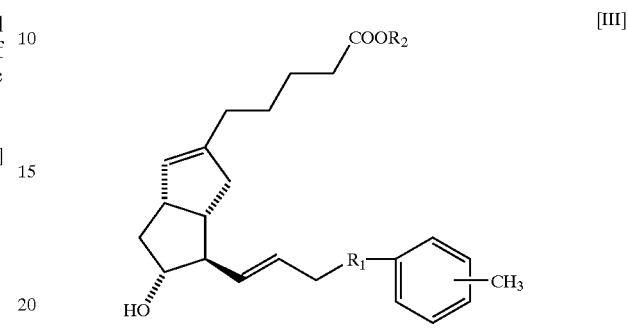

wherein, $R_1$ represents a $C_1$–$C_6$ alkylene group, and $R_2$ represents a hydrogen atom, a $C_1$–$C_7$ alkyl group or a protective group.

6. A method of treating a neurodegenerative disease according to claim 5, said method comprising administering to a subject in need of treatment a 15-deoxy-16-(m-tolyl)-17,18,19,20-tetranorisocarbacycline represented by the following formula [IV] or its methyl ester form:

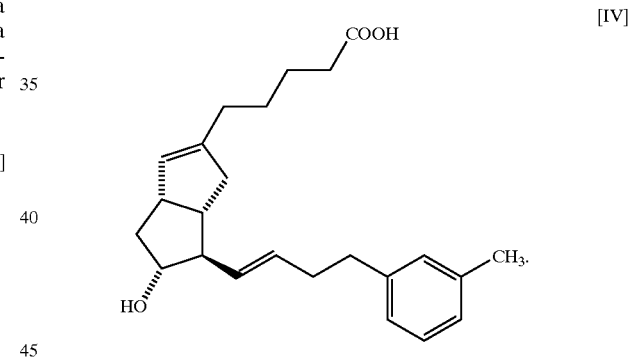

7. A method of treating a neurodegenerative disease according to claim 5 or 6, wherein said neurodgenerative disease is a degenerative disease that presents dementia symptoms.

8. A method of treating a neurodegenerative disease according to claim 5 or 6, wherein said neurodegenerative disease is Alzheimer's disease.

* * * * *